United States Patent
Mettes

(10) Patent No.: US 7,906,339 B2
(45) Date of Patent: Mar. 15, 2011

(54) SYSTEM AND METHOD FOR DETERMINING IMPURITY CONTENT IN A LIQUID

(76) Inventor: Jacob Mettes, Boulder, CO (US)

( * ) Notice: Subject to any disclaimer, the term of this patent is extended or adjusted under 35 U.S.C. 154(b) by 0 days.

(21) Appl. No.: 12/762,238

(22) Filed: Apr. 16, 2010

(65) Prior Publication Data

US 2010/0204926 A1 Aug. 12, 2010

Related U.S. Application Data

(63) Continuation of application No. 11/083,410, filed on Mar. 18, 2005, now abandoned, which is a continuation of application No. PCT/US03/29961, filed on Sep. 23, 2003.

(60) Provisional application No. 60/413,001, filed on Sep. 23, 2002.

(51) Int. Cl.
G01N 25/00 (2006.01)

(52) U.S. Cl. ......... 436/147; 204/408; 324/438; 324/439; 422/82.02; 422/82.12; 436/150; 700/266; 700/267; 702/30

(58) Field of Classification Search ................... 73/1.02, 73/1.03, 61.41, 61.61, 61.71, 863.01, 863.11; 73/61.46; 210/96.1, 96.2, 143, 149, 742, 210/746; 324/439, 441, 438; 422/62, 68.1, 422/82.02, 82, 12, 82.12; 700/266–273; 702/22, 23, 25, 85, 99, 127, 130, 30; 436/8, 436/9, 43, 50, 55, 147, 149, 150, 174, 146; 204/405, 408, 443, 433
See application file for complete search history.

(56) References Cited

U.S. PATENT DOCUMENTS

| | | | |
|---|---|---|---|
| 4,616,308 A | 10/1986 | Morshedi et al. | |
| 4,626,413 A | 12/1986 | Blades et al. | |
| 4,666,860 A | 5/1987 | Blades et al. | |
| 4,682,113 A | 7/1987 | Barben, II | |
| 4,775,634 A | 10/1988 | Sienkiewicz | |
| 4,939,921 A * | 7/1990 | Carter et al. | 73/1.03 |
| 5,272,091 A | 12/1993 | Egozy et al. | |
| 5,468,088 A | 11/1995 | Shoemaker et al. | |
| 5,518,933 A * | 5/1996 | Ishibashi | 436/163 |
| 5,779,911 A * | 7/1998 | Haug et al. | 210/739 |
| 5,872,454 A * | 2/1999 | West | 324/439 |
| 6,029,157 A | 2/2000 | Mihatsch | |
| 6,577,134 B2 * | 6/2003 | Farruggia et al. | 324/425 |
| 6,884,356 B2 | 4/2005 | Kosenka et al. | |
| 7,050,863 B2 | 5/2006 | Mehta et al. | |
| 7,254,564 B2 | 8/2007 | Coppola, Jr. et al. | |
| 2002/0103548 A1 | 8/2002 | Treiber et al. | |

* cited by examiner

*Primary Examiner* — Joseph W Drodge
(74) *Attorney, Agent, or Firm* — Standley Law Group LLP

(57) ABSTRACT

A system and method that uses electrical conductivity measurements to identify the impurities in a solution, as well as the concentrations of such impurities. The conductance versus temperature curve for any particular ion is unique to that ion and the conductance versus temperature curve for a solution is unique to the ions in the solution and their concentrations. Equations can be used to describe the conductivity versus temperature curve containing specific ions at set concentrations. To that end, the present invention measures the conductivity of a solution over some specified temperature range, calculates a conductivity-temperature curve from a library of ions to match the measured conductivity, and uses a mathematical process to vary the ions and their concentrations in the calculated curve to make it match the measured curve as closely as possible. If the match is close enough, the ions and their concentrations in the calculated curve will be taken as the ions and their concentrations in the measured solution.

18 Claims, 2 Drawing Sheets

SYSTEM AND METHOD FOR DETERMINING IMPURITY CONTENT IN A LIQUID

CROSS-REFERENCE TO RELATED APPLICATIONS

This application is a continuation of U.S. patent application Ser. No. 11/083,410, filed on Mar. 18, 2005, which is a continuation of PCT/US2003/029961, filed on Sep. 23, 2003 which, in turn, is entitled to benefit of a right of priority from U.S. Patent Application Ser. No. 60/413,001, filed on Sep. 23, 2002.

TECHNICAL FIELD

The present invention is directed to system and method for determining the impurity content in a liquid. More particularly, the present invention is directed to system and method capable of determining the impurity content in a liquid, as well as the concentrations of said impurities.

BACKGROUND

While a system and method of the present invention are not necessarily limited to the analysis of a single type of liquid, one skilled in the art should find it apparent that a system and method of the present invention may be particularly useful when employed for water analysis. As is well known, large quantities of water are used in industry, with quality levels ranging from "ultra pure" in applications such as semiconductor and pharmaceutical manufacturing, to "pure" in power generation, down to the lesser purity levels required of drinking and waste water treatment.

Regardless of the particular purity level required, however, all such water-consuming applications nonetheless need to be analyzed for purity. As would be understood by one of skill in the art, the large number of potential contaminants is a major complicating factor in such a water purity analysis.

Various devices and methods for analyzing the purity of water are known. For example, there exist laboratory-type instruments capable of scanning a multitude of chemical species with low detection limits. These laboratory-type instruments typically rely on grab samples of water that are subsequently analyzed in a central laboratory. For example, semiconductor fabrication operations might have permanent lines going to sample points, which enables the performance of a number of daily purity measurements daily with little sampling contamination. Conversely, drinking and waste water are typically sampled at two week periods.

One exemplary laboratory-type water purity analysis technique is ion chromatography. Ion chromatography makes use of an ion chromatograph laboratory instrument that can operate to separate the different ions of a water sample by their species specific elution time, which is measured after injection of a small amount of analyte into a column. Such ion chromatograph instruments may have many types of columns (each column specific to certain ions only) and need frequent calibration for each species to be analyzed.

Another exemplary laboratory-type water purity analysis technique involves the use of inductively coupled plasma (ICP). In this technique, a nebulizer injects an analyte into a gas (e.g., argon or helium) stream. A plasma is thereby created in the gas stream, which may be followed by the observation of the associated optical emission spectrum (in an ICP-OES techniques), or by routing of ions in the plasma into a mass spectrometer (in an ICP-MS technique).

Various laboratory-type techniques and instruments for performing water quality analysis are known. However, all such techniques and the associated laboratory-type instruments used therein share the common disadvantages of being very labor intensive, requiring high operating costs, a high initial investment, and frequent calibration.

More efficient online-type instruments are also known, but typically monitor one specific contaminant only. For example, to analyze relatively high impurity concentrations, a number of colorimetric or luminescence based techniques that use specific chemicals to create color change or light emitting reactions may be employed. Typically, a separate online-type instrument is required for each chemical species to be monitored. In addition to limitations in detection limits, these techniques are typically also not rigorously specific for a single species and involve often-delicate controlled flows of costly consumable chemicals. However, these techniques do typically feature fast response times.

Monitoring water properties such as Total Organic Carbon (TOC) is highly relevant in a number of important industrial processes—particularly in the semiconductor and pharmaceutical industries, which both use ultrapure water in large quantities. To this end, TOC analyzers are also available, and typically function to address contamination by organic species. As would be well-known to one of skill in the art, most TOC analyzers operate by oxidizing organic molecules in analyte water using UV radiation (see, e.g., U.S. Pat. No. 4,626,413). The $CO_2$ produced by oxidizing the organic molecules is then used as a measure of the organics in the analyte. However, if the UV oxidation releases conductive ions other than $CO_2$, then this method may be in error.

Further available are relatively inexpensive yet robust conductivity sensors, which are used online as a non-specific indicator of overall water quality. Such conductivity sensors feature a fast response time and high sensitivity. Consequently, conductivity and resistivity measurements are the most common, reliable, sensitive, accurate, and low-cost means of monitoring water purity for typical mineral contamination. One disadvantage of such conductivity sensors is the lack of information provided thereby in regard to the nature of detected contamination. That is, a typical conductivity measurement is the sum of the conductivities of all the ions in the solution and, therefore, does not reveal what ions are in the solution or the concentrations thereof. Another disadvantage of such conductivity sensors involves the dependency of the conductivity of the water on its temperature. Specifically, the electrical conductivity of a solution is extremely temperature dependent. This temperature dependence is further dependent on the types of ions in the solution. For this reason, conductivity measurements are typically temperature compensated to a standard temperature, typically 25° C.

SUMMARY OF THE GENERAL INVENTIVE CONCEPT

A system and method of the present invention overcomes the deficiencies of the aforementioned and known devices and associated analysis techniques. A system and method of the present invention uses known chemistry and conductivity equations to determine not just the nature of a chemical species (e.g., ions, dissolved gases, or neutral species) in a liquid (e.g., aqueous solution, liquid, or fluid) analyte, but also the concentrations thereof. For purposes of clarity, and not limitation, these chemical species will be referred to hereafter only as "ions" and the nature of exemplary analytes will be referred to hereafter only as being "liquid".

The analysis method of the present invention uses nonlinear curve fitting in determining the ions in an analyte and the concentrations of those ions. Since non-linear curve fitting may produce local minima that look like a solution, a wide scan technique may be used to find the global minima. The ion concentrations and the ions included in the analysis may then be stepped through a complete range of possible values to assure that the global (best) solution is found.

As an analysis method of the present invention requires knowledge of the specific conductance of any ion used in the analysis, the present invention also makes use of reverse fitting. The specific conductance of a particular ion can be the unknown in the analysis. By analyzing a solution of that ion at a known concentration, the specific conductance of that ion will be obtained as a function of temperature.

A system and method of the present invention can be designed to analyze the electrical conductivity of a solution of interest. As mentioned above, the electrical conductivity of a liquid solution is the sum of the conductivities of all the ions in the solution. By using the temperature dependence of the conductivity, the present invention is able to identify the particular ions present in the solution, as well as the concentrations thereof.

Conductivity sensors may be used in performing such a conductivity analysis. Most conductivity sensors contain two or four conductivity measuring electrodes and a temperature sensor. Both the conductivity electrodes and the temperature sensor need to be calibrated to make accurate measurements. The offset and span calibration factors for the conductivity electrodes and the temperature sensor can be variables determined in an analysis according to the present invention.

As discussed above with respect to TOC analysis techniques, irradiating a water sample with UV light will oxidize the organics in the sample to their basic components. The carbon present in the sample will come out as $CO_2$ (carbonic acid), which may be used as a measure of the organic concentration. By performing an analysis method of the present invention both before and after UV irradiation in a TOC analysis process, the increase in $CO_2$ produced by UV irradiation may be used to measure the total organic content of the sample. Further, any other conductive ions that are found to have appeared after the UV irradiation will be indicative what types of organics were present in the sample.

As would be well known to one of skill in the art, pH is very difficult to measure in ultra pure water. Determining the pH of ultra pure water requires determining the hydrogen ion content of the sample. The analysis performed according to the present invention determines the hydrogen ion content and, thus, the pH of ultra pure water may also be measured.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

A system and method of the present invention may be used to identify certain components (e.g., ions) of a liquid solution (e.g., water) and the concentrations of those components. Such a system of the present invention may include for example, and without limitation, one or more conductivity sensors (i.e., conductivity electrodes and a temperature sensor) and associated measurement electronics, a liquid flow system with flow control, a temperature control apparatus and an associated device for adjusting the temperature of the liquid in the system (typically between about 0° C. to 100° C.), one or more UV lamps for irradiating the liquid, and data processing and display hardware (e.g., a standard PC or built-in computer hardware).

Figure 1:
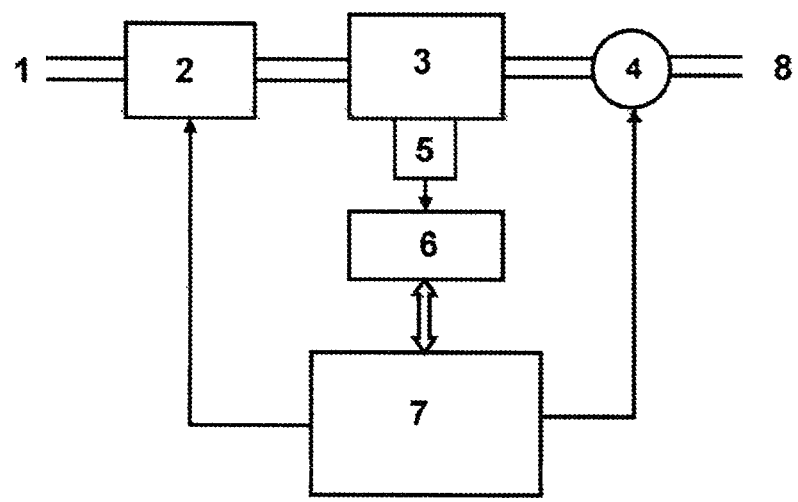
FIG. 1 is a schematic diagram of an exemplary automated analytical device of the present invention, which device may be used to implement an analysis method of the present invention that employs a mathematical model and non-linear curve fitting.

A simplistic block diagram of an exemplary embodiment of the present invention is illustrated in FIG. 1. As shown, a fluid input 1 is provided to a measurement/analysis system for introducing a liquid sample thereto. A sample preparation portion 2 of the system is provided to allow for optional preconditioning of the sample. A sample holding portion 3 of the system is provided to hold the sample while a conductivity vs. temperature measurement is made. A temperature control apparatus is associated with sample holding portion 3 of the system for controlling the temperature of the liquid in the system. A flow control and monitoring device 4 is provided to monitor and control the flow of the sample through the system.

The system is also provided with a sensor array 5. The sensor array 5 may be a single conductivity sensor (i.e., assembly of multiple conductivity electrodes and a temperature sensor), or it might be multiple conductivity sensors. The electrical conductivity electrodes of the conductivity sensor(s) may be separate from the associated temperature sensors, or it may be possible to integrate the electrical conductivity electrodes and a temperature sensor into a single device. In any event, the sensor array 5 is operable to measure the conductivity and temperature of a liquid sample while the sample is located in the holding portion 3 of the system.

A data acquisition system 6 for collecting conductivity and temperature data associated with the sample is also provided. Data from the data acquisition system 6 is sent to a data processing, display and control system 7. The data acquisition system 6 may simply be an interface between the conductivity sensor(s) and the data processing, display and control system 7. Alternatively, the data acquisition system 6 may be a more complex device that may provide data storage functionality or other functions.

General System Operation

The system of FIG. 1 may be operated to measure the conductivity and temperature of a liquid sample to be analyzed over some temperature range. This conductivity/temperature data is fed to the data processing, display and control system 7, which may be a microprocessor-based device such as a PC or similar computer. A computer program associated with the microprocessor-based device then calculates a conductivity vs. temperature curve that matches the measured curve obtained from measurements of the sensor array 5. The particular ions included in the calculated curve can be varied by the operator or varied automatically by the computer program. The computer program compares the calculated curve to the measured curve and, using standard mathematical techniques, varies parameters in the calculated curve to minimize the difference between (fit) the two curves. When the two curves match (converge) to within some predetermined degree, the parameters used in the computer calculated curve are displayed as the physical properties of the liquid (i.e., the ions and their concentrations) and/or system (conductivity cell calibration, for example).

Electrical Conductivity

The conductivity of liquid analytes will be measured over some temperature range, typically within a range of 0° C. to 100° C. For dilute solutions the conductivity as a function of temperature, σ(T), can be expressed as:

$$\sigma(T) = \Sigma_i c_i(T) * \lambda_i(T) \qquad \text{(Equation 1)}$$

where $c_i(T)$ is the concentration of ion i and $\lambda_i(T)$ is the specific ionic conductance of ion i. Both the concentration and specific conductance may vary with temperature.

If $\lambda_i(T)$ is unique for each ion in the solution, then σ(T) will be unique. Thus, for any measured σ(T) a mathematical solution for the right hand side of Equation 1 should exist that determines the concentrations of the ions in the solution.

Ion Analysis

The general approach for an ion analysis is to start with the charge balance equation. The contribution for each ion can be written in terms of its total chemical concentration, its dissociation constant and the hydrogen ion concentration [H$^+$].

An iterative approach is used to build up a polynomial expression in [H$^+$] that can be solved numerically by a computer program. The resulting value of [H$^+$] can then be used to find values for the concentrations of the involved ionized species. These values can then be used to calculate the conductivity of the solution.

Building up a polynomial generally involves the following steps: (1) starting with a second order polynomial representing ultra pure water (UPW) (see Equation 5); (2) adding the fully ionized strong acids and bases in the next step, modifying the second order polynomial; (3) adding one by one the weak acids whose dissociation involves only a single ionized species, with each addition increasing the order of the polynomial by one and thus producing a new series of polynomial coefficients based on the values of the coefficients of the previous polynomial; (4) adding the weak bases whose dissociation involves only a single ionized species, in a similar manner as the weak acids were added; (5) adding one by one the weak acids whose dissociation involves a single and a double ionized species, with each addition increasing the order of the polynomial by two and with each addition producing a new series of polynomial coefficients based on the values of the coefficients of the previous polynomial; (6) adding the weak bases whose dissociation involves a single and a double ionized species, in a similar way as the weak acids whose dissociation involves a single and a double ionized species; and (7) solving the polynomial for [H$^+$] and substituting the found value in the expressions for the concentrations of [WAS$^-$], [WBS$^+$], [WAD$^-$], [WAD$^{2-}$], [WBD$^+$], [WBD$^{2+}$]; where [WAS$^-$] is the concentration of a weak acid ion where the acid is only singularly ionized; [WBS$^+$] is the concentration of a weak base ion where the base is only singularly ionized; [WAD$^-$] is the concentration of the first weak acid ion of a doubly ionized acid; [WBD$^+$] is the concentration of the first weak base ion of a doubly ionized base; [WAD$^{2-}$] is the concentration of the second weak acid ion of a doubly ionized acid; and [WBD$^{2+}$] is the concentration of the second weak base ion of a doubly ionized base.

Water with no Additional Salts, Acids or Bases

The dissociation of water may be written as:

$$[H^+]*[OH^-] = k_w \qquad \text{(Equation 2)}$$

where [H$^+$] is the concentration of the hydrogen ion, [OH$^-$] is the concentration of the hydroxyl ion, and $k_w$ is the dissociation constant of water.

Conservation of charge gives:

$$[H^+] = [OH^-] \qquad \text{(Equation 3)}$$

Combining these two we have the initial polynomial in [H+]

$$[H^+] = \frac{k_w}{[H^+]} \qquad \text{(Equation 4)}$$

which can be rewritten as:

$$\frac{[H^+]^2}{[H^+]} = \frac{k_w}{[H^+]} \text{ or } \frac{[H^+]^2 - k_w}{[H^+]} = 0 \qquad \text{(Equation 5)}$$

In all cases the charge balance equation will be written as a ratio of polynomials in [H$^+$]:

$$\frac{P_0 + P_1*[H^+] + P_2*[H^+]^2 + \ldots + P_N*[H^+]^N}{Q_1*[H^+] + Q_2*[H^+]^2 + Q_3*[H^+]^3 + \ldots Q_{N-1}*[H^+]^{N-1}} = 0 \qquad \text{(Equation 6)}$$

For water only: $P_0 = -k_w$, $P_1 = 0$, $P_2 = 1$, $Q_1 = 1$

Water Plus a Strong Acid

Strong acids dissociate completely. The equation for this reaction is:

$$[sa] \rightarrow [H^+] + [sa^-] \qquad \text{(Equation 7)}$$

where [sa]=[sa$^-$]; [sa] is the concentration of the acid material (e.g., chlorine for hydrochloric acid, HCl); and [sa$^-$] is the concentration of the acid anion (e.g., chloride for hydrochloric acid)

Upon adding a strong acid with concentration [sa$_1$] to water, the charge balance equation becomes $$[H^+] = [OH^-] + [sa_1^-] \qquad \text{(Equation 8)}$$

Substituting for [OH—] from Equation 2 gives:

$$[H^+] = \frac{k_w}{[H^+]} + [sa_1^-] \qquad \text{(Equation 9)}$$

Rearranging this equation and using a common denominator gives:

$$\frac{[H^+]^2 - [sa_1^-]*[H^+] - k_w}{[H^+]} = 0 \qquad \text{(Equation 10)}$$

And the new polynomial coefficients are:

$P_0' = P_0$ $P_1' = P_1 - [sa_1^-]$ $P_2' = P_2$ $Q_1' = Q_1$

Water Plus a Strong Base, Weak Acids and Bases, and Doubly Ionized Acids and Bases The charge balance equation can be similarly built up as strong bases, weak acids and weak bases, and doubly ionized acids and bases are added to the solution. The ion dissociation equation and a conservation of mass equation for each acid or base is used to solve for the concentration of the particular ion in solution. This concentration is then put into the charge balance equation and new polynomial coefficients, $P_n$ and $Q_n$, are generated.

The starting equations for a strong base are:

$$[sb] \rightarrow [sb^+] + [OH^-] \qquad \text{(Equation 11)}$$

where $[sb]=[sb^+]$; $[sb]$ is the concentration of the base material (e.g., sodium for sodium hydroxide, NaOH); and $[sb^+]$ is the concentration of the base cation (e.g., sodium for sodium hydroxide).

The starting equations for a weak acid are:

$$[H^+]*[WAS^-] = k_{was}*[WAS] \qquad \text{(Equation 12)}$$

$$\text{where } [was] = [WAS] + [WAS^-] \qquad \text{(Equation 13)}$$

and where $[was]$ is the total concentration of the weak acid material (e.g., acetate for acetic acid); $[WAS]$ is the concentration of dissolved acid; $[WAS^-]$ is the concentration of the acid ion; and $k_{was}$ is the dissociation constant for the weak acid.

These equations give:

$$[WAS^-] = \frac{[was]}{\frac{[H^+]}{k_{was}} + 1} \qquad \text{(Equation 14)}$$

The starting equations for a weak base are:

$$[WBS^+]*[OH^-] = k_{wbs}*[WBS] \qquad \text{(Equation 15)}$$

$$\text{where } [wbs] = [WBS] + [WBS^+] \qquad \text{(Equation 16)}$$

and where $[wbs]$ is the total concentration of the weak base material; $[WBS]$ is the concentration of dissolved base; $[WBS^-]$ is the concentration of the base ion; and $k_{wbs}$ is the dissociation constant for the weak base.

These equations give:

$$[WBS^+] = \frac{k_{wbs}*[wbs]*[H^+]}{k_w + k_{wbs}*[H^+]} \qquad \text{(Equation 17)}$$

The starting equations for a doubly ionized weak acid (dissociation of weak acids with a single and a double ionized species) are:

$$[H^+]*[WAD^-] = k_{1wad}*[WAD] \qquad \text{(Equation 18)}$$

$$\text{and } [H^+]*[WAD^{2-}] = k_{2wad}*[WAD^-] \qquad \text{(Equation 19)}$$

$$\text{where } [wad] = [WAD] + [WAD^-] + [WAD^{2-}] \qquad \text{(Equation 20)}$$

These equations give:

$$[WAD^-] = \frac{[wad]*[H^+]}{\frac{[H^+]^2}{k_{1wad}} + [H^+] + k_{2wad}} = \qquad \text{(Equation 21)}$$

$$\frac{k_{1wad}*[wad]*[H^+]}{[H^+]^2 + k_{1wad}*[H^+] + k_{1wad}*k_{2wad}}$$

$$[WAD^{2-}] = \frac{k_{2wad}*[wad]}{\frac{[H^+]^2}{k_{1wad}} + [H^+] + k_{2wad}} = \qquad \text{(Equation 22)}$$

$$\frac{k_{1wad}*k_{2wad}*[wad]}{[H^+]^2 + k_{1wad}*[H^+] + k_{1wad}*k_{2wad}}$$

The factor that will be added to the conservation of charge equation for a doubly ionized weak acid will be:

$$[WAD^-] + 2*[WAD^{2-}] = [wad]* \qquad \text{(Equation 23)}$$

$$k_{1wad} * \frac{[H^+] + 2*k_{2wad}}{[H^+]^2 + k_{1wad}*[H^+] + k_{1wad}*k_{2wad}}$$

The starting equations for a doubly ionized weak base (dissociation of weak bases with a single and a double ionized species) are:

$$[WBD^+]*[OH^-] = k_{1wbd}*[WBD] \qquad \text{(Equation 24)}$$

$$\text{and } [WBD^{2+}]*[OH^-] = k_{2wbd}*[WBD^+] \qquad \text{(Equation 25)}$$

$$\text{where } [wbd] = [WBD] + [WBD^+] + [WBD^{2+}] \qquad \text{(Equation 26)}$$

These equations give:

$$[WBD^+] = \frac{k_w * k_{1wbd} * [wbd] * [H^+]}{k_w^2 + k_w * k_{1wbd} * [H^+] + k_{1wbd} * k_{2wbd} * [H^+]^2} \qquad \text{(Equation 27)}$$

$$[WBD^{2+}] = \frac{k_{1wbd} * k_{2wbd} * [wbd] * [H^+]^2}{k_w^2 + k_w * k_{1wbd} * [H^+] + k_{1wbd} * k_{2wbd} * [H^+]^2} \qquad \text{(Equation 28)}$$

The factor that will be added to the conservation of charge equation for a doubly ionized weak base will be:

$$[WBD^+] + 2*[WBD^{2+}] = [wbd]*k_{1wbd}*[H^+]* \qquad \text{(Equation 29)}$$

$$\frac{1 + 2 * \frac{k_{2wbd}}{k_w} * [H^+]}{k_w + k_{1wbd} * [H^+] + \frac{k_{1wbd}*k_{2wbd}}{k_w} * [H^+]^2}$$

Analysis

The analysis for the ion concentrations uses a non-linear least squares method. The analysis program requires some starting set of ions and concentrations. The operator has options for setting these starting conditions. For example, the operator may know what ions are in the sample, or could be in the sample, and their approximate concentrations. The operator could then use this information as the starting point for the analysis. If the analysis is an online analysis of some liquid system, then the results of an immediately preceding analysis can be used as the starting point for the next analysis.

If nothing is known about a liquid to be analyzed, then the apparatus can perform what may be referred to as a wide scan analysis. In this case, the analysis program generates many starting points with different combinations of ions in the solution. For each of these combinations, the program steps through a range of concentrations for each of the ions. The upper range for each ion is set by the measured conductivity, assuming that the solution contains only that ion. The program does an analysis for each of these starting points and subsequently selects the best fit from all of the analyses as the result.

Mathematical models for this analysis are described below. These mathematical methods converge to a minimum in a multidimensional space. This space may contain a number of minima. The goal is to find the best fit for the ion concentrations (i.e., the global minima). However, given a particular starting point, the analysis may converge on a local minima rather than the global minima. By performing a wide scan with fine enough concentration steps, this problem may be avoided and finding of the global minima can be guaranteed.

For a continuous analysis of a liquid, the global minima serves as an excellent starting point for the next analysis. Nonetheless, a wide scan should be performed periodically to assure that the analysis is still giving the best result.

To describe an ionic solution of water with low concentrations of strong acids, strong bases, singly and doubly ionized weak acids and singly and doubly ionized weak bases, the charge balance equation is constructed by starting with the equation for water (Equation 5), adding the acids and bases one at a time, and calculating the new $P_r$'s and $Q_s$'s for each addition.

The equation may be written as:

$$\frac{\sum_{r=0}^{N} P_r * [H^+]^r}{\sum_{s=1}^{N-1} Q_s * [H^+]^s} = 0 \quad \text{(Equation 30)}$$

where all of the k factors (the dissociation constants) are functions of temperature and, thus, the $P_r$'s and $Q_s$'s are functions of temperature.

For Equation 30 to be true:

$$\sum_{r=0}^{N} P_r * [H^+]^r = 0 \quad \text{(Equation 31)}$$

A pH transformation ($[H^+]=e^{pX}$) is used in Equation 31 and then Equation 31 is solved for pX. The transformation guarantees that $[H^+]$ will be positive. A mathematical method such as Newton-Raphson or Newton-Raphson with bisection may be used to solve for pX. The value of $[H^+]$ is then plugged back into the appropriate equations for the concentration of each acid or base.

The above procedure gives the concentrations of all ionic species as a function of temperature. Electrical conductivity as a function of temperature is then obtained by inserting these ionic concentration values and known values of the $\lambda_i$'s (which are also functions of temperature) into Equation 1. This equation for the electrical conductivity is exact for the ions taken to be in the solution and their concentrations.

Algorithms such as Levenberg-Marquardt or full Newton-type methods may be used with this conductivity function to vary the ion concentrations so that the calculated curve converges to the measured curve. These routines not only return the ion concentrations but also a quality of fit number that indicates how well the calculated curve agrees with the measured curve. If the quality of fit number is not acceptable then the ions in the analysis, their concentration range, or the step in concentration size in a wide scan, can be changed in an attempt to produce a better fit.

Other features of the solution being analyzed may be included in the equations for conductivity. Non-limiting examples of such features that may be included are interactions between ions when the concentrations are high, and ion concentration varying with time.

Since the ionic concentration analysis must include the concentration of the Hydrogen ion, the measurement of pH is included in the analysis. This is a great step forward in measurement technology as the measurement of pH in ultrapure water has been extremely difficult, if not impossible, to measure using standard pH measurement technologies.

A system and method of the present invention may also be used to measure total organic carbon (TOC) in a liquid (e.g., water) sample. If the sample to be analyzed is exposed to the light from a UV lamp, then the UV radiation will convert the organics in the sample to carbon dioxide. The carbon dioxide in the water sample immediately becomes carbonic acid. The change in carbonic acid ions before and after exposure to the UV light is directly related to the amount of organic material in the sample.

Known TOC measuring techniques are problematic because nitrogen-containing and halide-containing organics like urea and trihalomethanes (THMs) present in a liquid sample may produce other conductive ions in addition to the carbonic acid when exposed to UV light. Thus, using the conductivity change as a measurement of carbon dioxide may be in error because of the presence of such additional conductive ions. However, because the present invention will also identify non-carbonic acid conductive ions (e.g., urea-based or THM-based ions) present in the sample, the true TOC content of a sample may be accurately determined.

Figure 2:
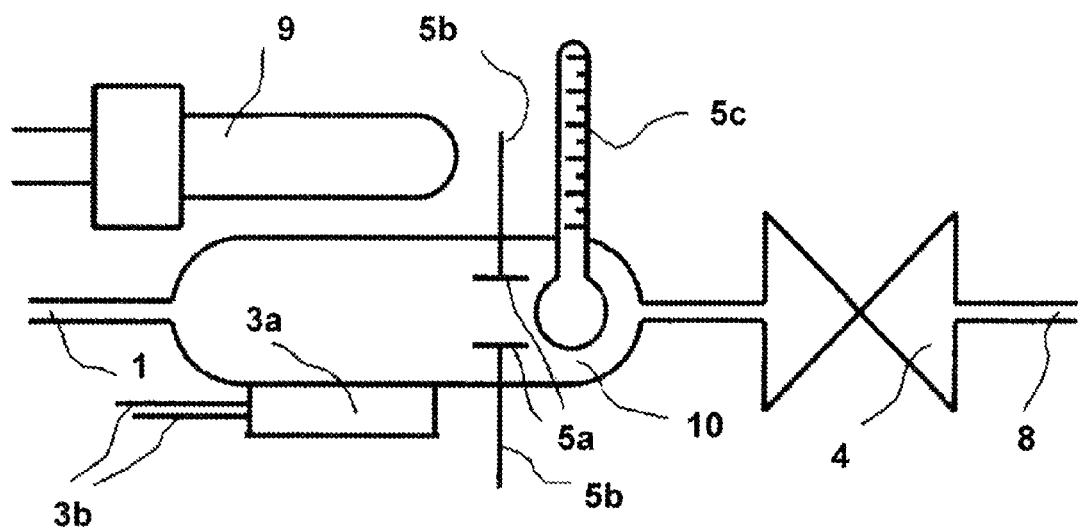
FIG. 2 depicts an exemplary stopped flow conductivity sensor with active temperature ranging.
Figure 3:
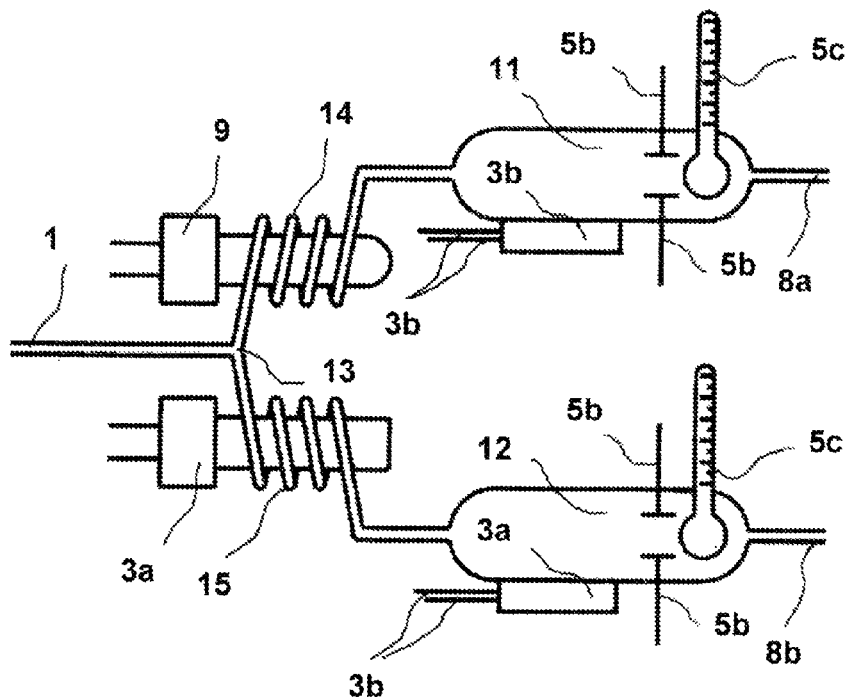
FIG. 3 illustrates an exemplary continuous flow application with two single downstream sensors.
Figure 4:
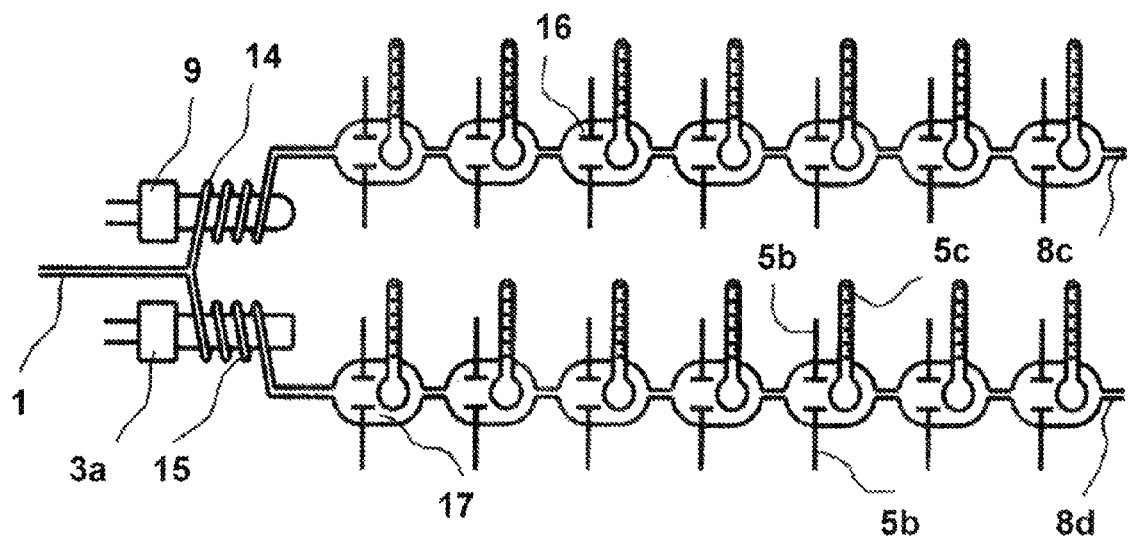
FIG. 4 shows an exemplary continuous flow application with sensor arrays.

More specific examples of sample preparation, temperature control, and conductivity and temperature measurement portions of a system of the present invention are depicted in FIGS. 2-4, and are described in more detail below.

An exemplary apparatus with a sensor array comprising non-temperature compensated conductivity sensors having conductivity electrodes $5a$, $5b$ for measuring the electrical conductivity of a liquid analyte and a temperature sensor $5c$ for measuring the temperature of the liquid analyte, is shown in FIG. 2. The apparatus is also shown to include a flow control device 4 that allows the analyte to enter a stopped flow cell 10 through a sample inlet 1. The flow control system 4 also operates to trap a sample of the analyte in the flow cell 10 and to permit removal of the analyte from the flow cell through an exit conduit 8. Such flow control devices and flow cells would be well known to one of skill in the art and need not be described in detail herein.

With the analyte sample trapped in the flow cell 10, the sample can be heated and/or cooled by a heating/cooling device $3a$ over some predetermined temperature range, typically about 0° C. to 100° C., but perhaps beyond this range for certain analytes. The heating/cooling device $3a$ may be connected to a temperature control device by leads $3b$. The conductivity and temperature of the sample are measured by the sensor array while the temperature is slowly swept over the temperature range under the management of the temperature control device. The temperature sensor $5c$ is calibrated so that it accurately measures temperature while the temperature is changing.

A computer program and microprocessor-based device of an associated data analysis, display and control system (see element 7 of FIG. 1) then calculates a conductivity vs. temperature curve for the liquid, with a specified ion content and concentration. An operator has the option of setting starting ion content and concentrations for the analysis, to let the program start the analysis with a preprogrammed configuration, or to allow the performance of a wide scan analysis. The ion content and concentrations are then varied by the program using a non-linear least squares fitting routine such as, without limitation, a Levenberg-Marquardt routine.

Once the best fit has been obtained, the program may display one or more of the ions searched for, the concentrations thereof, the pH of the analyte, and a quality of curve fit number. The operator can accept the analysis if the quality of curve fit number is acceptable, or the operator may reinitiate the analysis after reconfiguring the starting parameters. When the temperature sweep of the sample is complete, the flow control system 4 will allow the analyte to flow through the flow sensor 10 again to collect a new sample for the next analysis.

FIG. 3 illustrates another exemplary embodiment of the present invention. In this embodiment, an apparatus similar to the apparatus shown in FIG. 2 may be provided, but with one or more flow cells 11, 12 that permit a continuous flow of analyte to pass therethrough. Each flow cell 11, 12 may be equipped with its own sensor array 5a-5c. Some form of flow control may be included in this apparatus to regulate the rate of flow of analyte through the flow cell(s). Such an apparatus may be suitable for use in analyzing analytes with very stable chemical compositions. In such an embodiment, conductivity and temperature measurements are performed on an analyte as it flows at a controlled and continuous rate through the flow cells, as would be well understood by one of skill in the art.

In another exemplary embodiment of the present invention, an apparatus similar to the apparatus shown in FIG. 2 may be provided, but with multiple conductivity and temperature sensors (i.e., sensor arrays) arranged in series along the flow path of the analyte. Since each sensor in such an embodiment would be at a different temperature, simultaneous (concurrent) readings from the sensors may be used to substantially instantaneously produce a conductivity vs. temperature curve. The sensor array of such an embodiment might be implemented in a Micro-Electro-Mechanical System (MEMS) array, making for a small, fast and accurate system. FIG. 4 shows two series-arranged parallel multiple sensor arrays configured for a TOC analysis.

Exemplary apparatus of the present invention for use in measuring the TOC content of an analyte are depicted in FIGS. 2-4. These embodiments a trapped liquid sample to be exposed to UV light. The analyte analysis described above with respect to FIG. 1 can again be performed with regard to liquid analytes analyzed using these embodiments.

Referring to FIG. 2, the analyte flow cell 10 (sample chamber) is constructed of quartz or another acceptable material that allows UV light from a UV light source 9 to irradiate a sample of analyte located therein. The conductivity can be tracked over time during the UV exposure to determine the endpoint conductivity (when all of the organics have converted to carbon dioxide). The analysis can then be repeated. The difference in carbonic acid concentration between the first and second analyses may then be converted to a TOC concentration.

If the UV oxidation of the organics is incomplete, large organic ions will remain in the analyte. These will lead to a poor quality of curve fit if they are not included in the analysis. Thus a poor quality of fit dictates that either the sample is expose to the UV light source for a longer time period or that the organic ions are included in the analysis.

Referring now to FIG. 3, a supply conduit 1 comprising a tube of quartz or a similar material is used to supply analyte to the two flow cells (sample chambers) 11, 12. The conduit 1 includes a Y or T section 13 wherein the conduit splits into two separate legs 14, 15. The first leg 14 spirals around a UV light source 9, while the second leg 15 spirals around a heater 3a. The analyte flow is the same through both paths of the conduit. The analyte flows into both the flow cells 11, 12 via the conduit legs 14, 15. The analyte that travels through the first conduit leg 14 is exposed to UV light from the UV light source 9 prior to the time it enters the associated flow cell 11. Each of the flow cells 11, 12 is equipped with a sensor array 5a-5c. The difference between the carbonic acid readings obtained from the sensor arrays located in the two flow cells 11, 12 is used to calculate TOC. Analyte may be removed from the flow cells 11, 12 via associated exit conduits 8a, 8b.

Yet another exemplary embodiment of the present invention is depicted in FIG. 4. This embodiment is substantially similar to the embodiment shown in FIG. 3, except that a plurality of sensor arrays are arranged in parallel for measuring the temperature and conductivity of an analyte.

More particularly, analyte flows through the conduit 1 and through the separate conduit legs 14, 15 as described above, whereby the analyte traveling through the first conduit leg 14 is once again irradiated with UV light from the UV light source 9 and the analyte traveling through the second conduit leg 15 may be heated by the associated heater 3a. As with the embodiment of FIG. 3, the analyte flow is the same through both paths of the conduit. The analyte in each leg 14, 15 of the conduit respectively flows through multiple flow cells 16, 17 that are arranged in series along the flow path of the analyte. Each of the flow cells 16, 17 includes its own sensor array 5a-5c. The difference between the carbonic acid readings obtained from the sensor arrays located in the two series of flow cells 16, 17 is used to calculate TOC. Analyte may be removed from the flow cells 16, 17 via associated exit conduits 8c, 8d.

In still another embodiment of the present invention, a system such as the system schematically represented in FIG. 1, may be used with an analyte of known composition (i.e., of known ion content and concentration) to calibrate the conductivity measuring electrodes and the temperature sensor of the system. As an example, ultrapure water made with nuclear grade ion exchange resins would be an acceptable analyte. The cell constant of the conductivity cell and the span and offset factors for the temperature sensor would be the unknowns. The system could thus be used to calibrate the conductivity measuring electrodes and the temperature sensor.

While certain embodiments of the present invention are described in detail above, the scope of the invention is not to be considered limited by such disclosure, and modifications are possible without departing from the spirit of the invention as evidenced by the following claims:

What is claimed is:

1. A system for determining a chemical species, and the concentrations of said chemical species, present in an electrically conductive liquid analyte whose electrical conductivity is measurable as a function of its temperature, said system comprising:

at least one electrical conductivity sensor and at least one temperature sensor in contact with an analyte of interest, said sensors in communication with a data acquisition system that measures the electrical conductivity and temperature of said analyte at a plurality of temperatures;

a temperature control device adapted to vary the temperature of said analyte of interest while the electrical conductivity thereof is being measured by said data acquisition system;

a data acquisition system adapted to transfer measured electrical conductivity and temperature data from said data acquisition system to a microprocessor-based device; and a program that, in combination with said microprocessor-based device, is adapted to:

calculate electrical conductivity as a function of temperature given an ion composition of the analyte and given the concentrations and ionic conductance vs. temperature of the ions and the disassociation constants vs. temperature of an acid or base associated with each ion, compare measured electrical conductivity with calculated electrical conductivity at the plurality of temperatures, automatically vary the concentrations of the ions used in calculating electrical conductivity to minimize any difference between calculated electrical conductivity data and measured electrical conductivity data, and quantify the difference between calculated electrical conductivity data and measured electrical conductivity data to determine acceptability of the ion composition and the concentrations of the ions in the calculated data as the ions and concentrations of said ions in the analyte.

2. The system of claim 1, wherein said system is also adapted to determine the pH value of an analyte whenever a hydrogen ion is one of the ions included in the analysis.

3. The system of claim 1, further comprising a component for exposing an analyte to UV light and a component for determining total organic carbon (TOC) content by analyzing an increase in $CO_2$ concentration caused by exposing the analyte to UV light.

4. The system of claim 1, wherein said system is an online system that measures grab samples of analyte.

5. The system of claim 1, wherein said system is an online system that measures a flowing analyte.

6. The system of claim 1, wherein said program is adapted to start an analysis from a predetermined set of ions in said analyte and from predetermined concentrations of said ions, and to automatically step through an allowed concentration range for each ion and through all possible combinations of said predetermined set of ions.

7. The system of claim 1, wherein said program is adapted to generate data from multiple possible starting concentrations and combinations of ions and to automatically step through an allowed concentration range for each ion and through all possible combinations of ions until the difference between calculated and measured electrical conductivity is within some predetermined value.

8. A method for determining a chemical species, and the concentrations of said chemical species, present in an electrically conductive liquid analyte whose electrical conductivity is measurable as a function of its temperature, said method comprising:

providing the system of claim 1;
supplying an analyte of interest to said system; and
operating said system to analyze said analyte and to determine the ions and the concentrations of said ions in said analyte.

9. The method of claim 8, wherein said system includes a program that is further adapted to automatically vary the ions and the concentrations of the ions used in calculating electrical conductivity, and said ions and the concentrations of the ions are varied while calculating electrical conductivity so as to minimize any difference between calculated electrical conductivity data and measured electrical conductivity data.

10. The system of claim 1, wherein said program is further adapted to automatically vary the ions and the concentrations of the ions used in calculating electrical conductivity to minimize any difference between calculated electrical conductivity data and measured electrical conductivity data.

11. The system of claim 1, wherein said data acquisition system stores said measured electrical conductivity and temperature data.

12. The system of claim 1, wherein said program is adapted to start an analysis by generating data for multiple possible ions present in said analyte and for possible starting concentrations of said ions, and to automatically step through an allowed concentration range for each ion and through all possible combinations of said ions.

13. The system of claim 1, wherein said temperature control device varies the temperature of said analyte over some predetermined temperature range.

14. A method for determining a chemical species, and the concentrations of said chemical species, present in an electrically conductive liquid analyte whose electrical conductivity is measurable as a function of its temperature, said method comprising:

placing at least one electrical conductivity sensor and at least one temperature sensor in contact with an analyte of interest;

placing said at least one electrical conductivity sensor and at least one temperature sensor in communication with a data acquisition system to measure the electrical conductivity and temperature of said analyte at a plurality of temperatures;

using a temperature control device to vary the temperature of said analyte of interest while the electrical conductivity thereof is measured by said measurement electronics;

using said data acquisition system to transfer measured electrical conductivity and temperature data from said at least one electrical conductivity sensor and said at least one temperature sensor to a microprocessor-based device;

providing a software program, said software program in communication with said microprocessor-based device;

using said program, in combination with said microprocessor-based device, to:

calculate electrical conductivity as a function of temperature given an ion composition of the analyte and given the concentrations and ionic conductance vs. temperature of the ions and the disassociation constants vs. temperature of an acid or base associated with each ion, compare measured electrical conductivity with calculated electrical conductivity at the plurality of temperatures, automatically vary the concentrations of the ions used in calculating electrical conductivity to minimize any difference between calculated electrical conductivity data and measured electrical conductivity data, and quantify the difference between calculated electrical conductivity data and measured electrical conductivity data to determine acceptability of the ion composition and the concentrations of the ions in the calculated data as the ions and concentrations of said ions in the analyte.

15. The method of claim 14, further comprising using said program, in combination with said microprocessor-based device, to automatically vary the ions and the concentrations of the ions used in calculating electrical conductivity to minimize any difference between calculated electrical conductivity and measured electrical conductivity data.

16. The method of claim 14, wherein said data acquisition system stores said measured electrical conductivity and temperature data before or after transferring said data to said microprocessor-based device.

17. A system for determining a chemical species, and the concentrations of said chemical species, present in an electrically conductive liquid analyte whose electrical conductivity is measurable as a function of its temperature, said system comprising:
 at least one electrical conductivity sensor and at least one temperature sensor in contact with an analyte of interest, said sensors in communication with a data acquisition system that measures the electrical conductivity and temperature of said analyte at a plurality of temperatures;
 a temperature control device adapted to vary the temperature of said analyte of interest while the electrical conductivity thereof is being measured by said data acquisition system;
 a data acquisition system adapted to transfer measured electrical conductivity and temperature data from said data acquisition system to a microprocessor-based device; and
 a program that, in combination with said microprocessor-based device, is adapted to:
  start an analysis by generating data for multiple possible ions present in said analyte and for possible starting concentrations of said ions, and to automatically step through an allowed concentration range for each ion and through all possible combinations of said ions,
  calculate electrical conductivity as a function of temperature given an ion composition of the analyte and given the concentrations and ionic conductance vs. temperature of the ions and the disassociation constants vs. temperature of an acid or base associated with each ion,
  compare measured electrical conductivity with calculated electrical conductivity at the plurality of temperatures,
  automatically vary the concentrations of the ions used in calculating electrical conductivity to minimize any difference between calculated electrical conductivity data and measured electrical conductivity data, and
  quantify the difference between calculated electrical conductivity data and measured electrical conductivity data to determine acceptability of
  the ion composition and the concentrations of the ions in the calculated data as the ions and concentrations of said ions in the analyte.

18. The system of claim 17, wherein said program is adapted to automatically step through an allowed concentration range for each ion and through all possible combinations of ions until the difference between calculated and measured electrical conductivity is within some predetermined value.

* * * * *